United States Patent [19]

Sieger et al.

[11] 4,016,273
[45] Apr. 5, 1977

[54] SUSTAINED RELEASE FORMS OF CERTAIN OXAZEPINES FOR PARENTERAL ADMINISTRATION

[75] Inventors: George Madison Sieger, Montvale, N.J.; James Elwood Krueger, New City; Arnold Curtis Osterberg, Pearl River, both of N.Y.; David Henry Tedeschi, Little Falls, N.J.

[73] Assignee: American Cyanamid Company, Stamford, Conn.

[22] Filed: July 16, 1975

[21] Appl. No.: 596,488

[52] U.S. Cl. .............................................. 424/250
[51] Int. Cl.$^2$ ..................................... A11K 31/495
[58] Field of Search .............. 424/250; 260/268 TR

[56] References Cited

UNITED STATES PATENTS

| | | | |
|---|---|---|---|
| 3,164,520 | 1/1965 | Huber | 424/312 |
| 3,538,216 | 11/1970 | Polin | 424/312 |
| 3,546,220 | 12/1970 | Schmutz et al. | 424/258 |
| 3,549,621 | 12/1970 | Yole | 260/268 TR |
| 3,681,357 | 8/1972 | Howell et al. | 260/268 TR |
| 3,773,768 | 11/1973 | Howell et al. | 260/268 TR |
| 3,891,647 | 6/1975 | Schmutz et al. | 260/268 TR |

OTHER PUBLICATIONS

Martin – Remingtons's Pharmaceutical Sciences 13th Ed. pp. 627 and 634–636.

Primary Examiner—Stanley J. Friedman
Attorney, Agent, or Firm—Denis A. Polyn

[57] ABSTRACT

A sustained release depot form of the free base or pamoate salt of 2-chloro-11-(1-piperazinyl)-dibenz[b,f][1,4]-oxazepine or 2-chloro-11-(4-methyl-1-piperazinyl)-dibenz[b,f]-[1,4]oxazepine in an injectable oil for parenteral administration.

8 Claims, No Drawings

SUSTAINED RELEASE FORMS OF CERTAIN OXAZEPINES FOR PARENTERAL ADMINISTRATION

BACKGROUND OF THE INVENTION

Both 2-chloro-11-(piperazinyl)-dibenz[b,f][1,4]oxazepine and 2-chloro-11-(4-methyl-1-piperazinyl)-dibenz[b,f][1,4]oxazepine are known compounds having therapeutic effects on the central nervous system.

U.S. Pat. No. 3,546,226 specifically discloses the compound 2-chloro-11-(4-methyl-1-piperazinyl)-dibenz[b,f][1,4]oxazepine, and broadly discloses the compound 2-chloro-11-(piperazinyl)-dibenz[b,f][1,-4]oxazepine, their method of preparation, their non-toxic pharmaceutically acceptable acid addition salts and their utility as central nervous system agents. The '226 patent also discloses the parenteral administration of the above compounds. However, the '226 patent does not disclose sustained release forms of the above compounds as set forth herein.

U.S. Pat. No. 3,663,696 discloses the preparation and treatment of depression with 2-chloro-11-(1-piperazinyl)-dibenz[b,f][1,4]oxazepines and the acid addition salts thereof, including the hydrochloride, sulfate, phosphate, citrate, tartrate, maleate, succinate and fumarate. The '696 patent also discloses parenteral administration of the above compounds, and a specific parenteral solution of 2-chloro-11-(1-piperazinyl)-dibenz[b,f][1,4]oxazepine. However, the '696 patent does not disclose sustained release forms of the above compounds as set forth herein.

U.S. Pat. No. 3,194,733 discloses certain acid esters of phenothiazines useful as tranquilizing or ataractic agents such as the enanthate ester of fluphenazine. The '733 patent discloses the pamoate ester and parenteral formations comprising phenothiazine compounds and aluminum monostearate in vegetable oils or synthetic esters of long chain fatty acids. However, the pamoate of the present invention is not a phenothiazine or an acid ester, but the salt of a base, and is structurally different from the acid ester compounds disclosed in the '733 patent.

Prior to the present invention, there was no prolonged acting central nervous system formulation of 2-chloro-11-(1-piperazinyl)-dibenz[b,f][1,4]oxazepine or 2-chloro-11-(4-methyl-1-piperazinyl)-dibenz[b,f][1,4]oxazepine, in either the free base or pamoate salt forms. The present invention supplies such formulations. Formulations, capable of prolonged action and consequently less frequent administration, are much desired as they are more convenient and easier to use where continuous and uninterrupted administration is needed.

SUMMARY OF THE INVENTION

The invention is concerned with a pharmaceutical composition for parenteral administration characterized by prolonged duration of activity, which comprises, as the main active ingredient therein, the free base or the pamoate salt of either 2-chloro-11-(4-methyl-1-piperazinyl)-dibenz[b,f]-[1,4]oxazepine or 2-chloro-11-(1-piperazinyl)-dibenz[b,f]-[1,4]oxazepine in an injectable oil and, optionally, a gelling agent. The invention is also concerned with a method of treating central nervous system disorders in warm-blooded animals which comprises parenterally administering a therapeutically effective amount of the above compounds to mammals.

The compounds of the present invention have a pronounced therapeutic effect on the central nervous system. The compound 2-chloro-11-(4-methyl-1-piperazinyl)-dibenz[b,f][1,4]oxazepine is particularly active as a neuroplegic, neuroleptic, neuroleptic antidepressant, antimetic, analgesic and sedative. Further information on the central nervous system activity of the later compound can be found in U.S. Pat. No. 3,546,226. It is suitable as an anti-psychotic agent for the treatment of certain psychotic conditions, for example, schizophrenia. The compound 2-chloro-11-(1-piperazinyl)-dibenz[b,f][1,4]oxazepine also acts upon the central nervous system and is particularly active as an anti-depressant. Further information on the activity of this compound can be found in U.S. Pat. No. 3,663,696.

The compounds of this invention, either in the base form or as the pamoate salts, when incorporated in a formulation containing an injectable oil, with or without a gelling agent such as aluminum monostearate, provide a sustained release (depot) product when administered parenterally. For prolonged action, the compounds are formulated in an injectable oil, preferably a vegetable oil, as for example sesame oil, peanut oil, cottonseed oil, corn oil or soybean oil, or mixtures of these oils, or synthetic oils such as the glycerol or propylene glycol esters of long chain fatty acids. The active component is formulated at a concentration of about 50 mg./ml. to about 400 mg./ml. A gelling agent such as aluminum monostearate may be added to the oil to provide a final concentration of about 10 mg./ml. to about 100 mg./ml., the mixture may then be gelled by appropriate heat treatment. Other suitable gelling agents include aluminum distearate, aluminum tristearate and mixtures thereof; and the aluminum laurate, myristate, palmitate, and oleate salts, and mixtures thereof. The preferred parenteral mode of administration of these compositions is either intramuscular or subcutaneous.

DETAILED DESCRIPTION OF THE INVENTION

The following will illustrate the invention in more detail.

EXAMPLE 1

Preparation of a Parenteral Suspension of 2-Chloro-11-(4-methyl-1-piperazinyl)-dibenz[b,f][1,-4]oxazepine Base in Gelled Sesame Oil Containing Aluminum Monostearate A solution phase is prepared by dissolving 2.0 g. of 2-chloro-11-(4-methyl-1-piperazinyl)-dibenz[b,f][1,-4]oxazepine base in 30.6 ml. of gelled sesame oil containing 2% aluminum monostearate at 60° C., and then cooling.

The final suspension is prepared by placing 7.0 g. of 2-chloro-11-(4-methyl-1-piperazinyl)-dibenz[b,f][1,-4]oxazepine base is a mortar and gradually adding 15.3 ml. of the above solution phase while grinding with a pestle. The result is a thixotropic, but mobile suspension which may be drawn into a syringe and then filled in vials and sterilized.

Since 7.0 gm. of 2-chloro-11-(4-methyl-1-piperazinyl)-dibenz[b,f][1,4]oxazepine base occupies 4.7 cc, the final volume is 20 cc, giving a final concentration of 8 gm. of active component per 20 cc of the finished preparation. A 2 cc dose then delivers 800 mg.

In the same manner, 13.0 g. of the oxazepine base is mixed in a motar with 40.0 ml. of a 5.0% w/v solution of oxazepine base in gelled sesame oil to yield 50.0 ml. of a mixture containing 30.0% 2/v of oxazepine overall.

EXAMPLE 2

Preparation of a Parenteral Suspension of 2-Chloro-11-(1-piperazinyl)-dibenz[b,f][1,4]oxazepine Base in Gelled Peanut Oil Containing Aluminum Monostearate 2-Chloro-11-(1-piperazinyl)-dibenz[b,f][1,4]oxazepine base is placed in a mortar. Sufficient peanut oil, gelled with 2.5% aluminum monostearate, is added gradually, while thoroughly mixing and dispersing the solid in the liquid with a pestle, to make a suspension of the desired concentration (e.g. 40% w/v). The resulting suspension is viscous but mobile. The suspension may be loaded in syringes or vials and sterilized.

EXAMPLE 3

Preparation of a Parenteral Suspension of 2-Chloro-11-(1-piperazinyl)-dibenz[b,f][1,4]oxazepine, Salt with 4,4'-Methylenebis[3-hydroxy-2-naphthoic Acid] (2:1) in Gelled Sesame Oil Containing Aluminum Monostearate 2-Chloro-11-(1-piperazinyl)-dibenz[b,f][1,4]oxazepine salt with 4,4'-methylenebis[3-hydroxy-2-naphthoic acid] (2:1) is added to sesame oil gelled with 1.5% aluminum monostearate to make a final concentration of 20% 2/v as the base. The suspension is thoroughly dispersed by ultrasonic agitation for 5 minutes. The suspension may be loaded into syringes or vials and sterilized.

EXAMPLE 4

Preparation of a Parenteral Suspension of 2-Chloro-11-(4-methyl-1-piperazinyl)-dibenz[b,f][1,4]oxazepine, Salt with 4,4'-Methylenebis[3-hydroxy-2-naphthoic acid] (2:1) is Gelled Cotton Seed Oil Containing Aluminum Monostearate 2-Chloro-11-(4-methyl-1-piperazinyl)-dibenz[b,f]-[1,4]oxazepine, salt with 4,4'-methyelnebis[3-hydroxy-2-naphthoic acid] (2:1) is added to cotton seed oil gelled with 1.5% aluminum monostearate to make a final concentration of 10% w/v as base. The suspension is thoroughly mixed by ultrasonic agitation. The thixotropic suspension may be loaded into syringes or vials and sterilized.

EXAMPLE 5

Preparation of a Parenteral Suspension of 2-Chloro-11-(4-methyl-1-piperazinyl)-dibenz[b,f][1,4]oxazepine, Salt with 4,4'Methylenebis[3-hydroxy-2-naphthoic acid] (2:1) in Sesame oil 2-Chloro-11-(4-methyl-1-piperazinyl)-dibenz[b,f][1,4]oxazepine, salt with 4,4'-methylenebis[3-hydroxy-2-naphthoic acid] (2:1) is added to sesame oil to make a final concentration of 20% w/v as base. The suspension is thoroughly mixed and dispensed by ultrasonic agitation for 5 minutes, or until the mixture becomes warm. The suspension is loaded into vials and sterilized.

EXAMPLE 6

Preparation of a Parenteral Suspension of 2-Chloro-11-(4-methyl-1-piperazinyl)-dibenz[b,f][1,-4]oxazepine, Salt with 4,4'-Methylenebis[3-hydroxy-2-naphthoic acid] (2:1) in Gelled Peanut Oil Containing Aluminum Monostearate 2-Chloro-11-(4-methyl-1-piperazinyl)-dibenz[b,f][1,4]oxazepine, salt with 4,4'-methylenebis[3-hydroxy-2-naphthoic acid] (2:1) is added to peanut oil gelled with 2.5% aluminum monostearate to make a final concentration of 10% w/v as base. The suspension is thoroughly mixed by ultrasonic agitation. The thixotropic suspension may be loaded into syringes or vials and sterilized.

EXAMPLE 7

Preparation of a Parenteral Suspension of 2-Chloro-11-(4-methyl-1-piperazinyl)-dibenz[b,f][1,-4]oxazepine, Salt with 4,4'-Methylenebis[3-hydroxy-2-naphthoic acid] (2:1) in Gelled Sesame Oil Containing Aluminum Monostearate 2-Chloro-11-(4-methyl-1-piperazinyl)-dibenz[b,f][1,4]oxazepine, salt with 4,4'-methylenebis[3-hydroxy-2-naphthoic acid] (2:1) is added to sesame oil gelled with 1.0% aluminum monostearate to make a final concentration of 20% w/v as base. The suspension is dispersed by ultrasonic agitation for 5 minutes, or until the mixture becomes warm. The suspension is loaded into vials and sterilized.

EXAMPLE 8

Preparation of a Parenteral Suspension of 2-Chloro-11-(1-piperazinyl)-dibenz[b,f][1,4]oxazepine Base in Corn Oil 2-Chloro-11-(1-piperazinyl)-dibenz[b,f][1,4]oxazepine base is placed in a mortar. Sufficient corn oil is added gradually, while thoroughly mixing and dispersing the solid in the liquid with a pestle, to make a suspension of the desired concentration (e.g. 30% w/v). The resulting suspension is viscous but mobile. The suspension may be loaded in syringes or vials and sterilized.

EXAMPLE 9

Preparation of a Parenteral Suspension of 2-Chloro-11-(1-piperazinyl-dibenz[b,f][1,4]oxazepine, Salt with 4,4'-methylenebis[3-hydroxy-2-naphthoic acid] (2:1) in Sesame Oil 2-Chloro-11-(1-piperazinyl)-dibenz[b,f][1,4]oxazepine, salt with 4,4'-methylenebis[3-hydroxy-2-naphthoic acid] (2:1) is added to sesame oil to make a final concentration of 20% w/v as base. The suspension is dispersed by ultrasonic agitation for 5 minutes, or until the mixture becomes warm. The suspension is loaded into vials and sterilized.

EXAMPLE 10

Preparation of a Parenteral Suspension of 2-Chloro-11-(4-methyl-1-piperazinyl)-dibenz[b,f][1,4]oxazepine base, 10% in Sesame Oil Sesame oil is sterilized at 150° C. for 30 minutes and cooled aseptically. Benzyl alcohol (1.5%) is added aseptically to the sterile oil. 2-Chloro-11-(4-methyl-1-piperazinyl)-dibenz[b,f][1,4]oxazepine base is sterilized with ethylene oxide and added aseptically to the sterile sesame oil to give a final concentration of 10.5% w/v. The suspension is aseptically mixed, keeping the temperature of the suspension below 35° C., and aseptically filled into vials.

EXAMPLE 11

Preparation of a Parenteral Suspension of 2-Chloro-11-(4-methyl-1-piperazinyl)-dibenz[b,f][1,4]oxazepine, Salt with Hydrochloric Acid [1,1] in Cottonseed Oil 2-Chloro-11-(4-methyl-1-piperazinyl)-dibenz[b,f]-[1,4]oxazepine, salt with hydrochloric acid [1,1] is added to cottonseed oil to make a final concentration of 35% w/v as base. The suspension is dispersed by ultrasonic agitation for 5 minutes, or until the mixture becomes warm. The resulting suspension can readily by discharged through a 21-gauge needle.

EXAMPLE 12

Preparation of a Parenteral Suspension of 2-Chloro-11-(4-methyl-1-piperazinyl)-dibenz[b,f][1,4]oxazepine, Salt with Succinic Acid [1,1], in Gelled Corn Oil Containing Aluminum Monostearate 2-Chloro-11-(4-methyl-1-piperazinyl)-dibenz[b,f]-[1,4]oxazepine, salt with succinic acid [1,1] is added to corn oil gelled with 2.5% aluminum monostearate to make a final concentration of 25% 2/v as base. The suspension is thoroughly mixed by ultrasonic agitation for 5 minutes, or until the mixture becomes warm. The thixotropic suspension may be loaded into syringes or vials and sterilized.

In order to show the effectiveness of the sustained release formulations of the present invention the following tests were performed:

Formulations:

I 2-Chloro-11-(4-methyl-1-piperazinyl)-dibenz[b,f][1,4]oxazepine base in solution at a concentration of 2% in a 70% solution of propylene glycol in water, as a control.

II 2-Chloro-11-(4-methyl-1-piperazinyl)-dibenz[b,f][1,4]oxazepine pamoate in suspension at a concentration of 2.5% (as base) is gelled sesame oil containing 2% aluminum monostearate.

III 2-Chloro-11-(4-methyl-1-piperazinyl)-dibenz[b,f][1,4]-oxazepine pamoate in suspension at a concentration of 2.5% (as base) in sesame oil.

IV Prolixin®[1] enanthate [4-{3-[2-(trifluoromethyl)-phenothiazin-10-yl]propyl}-1-piperazine-ethanol heptanoate (enanthate)], hereinafter fluphenazine enanthate, in solution at a concentration of 2.5% in sesame oil.

[1]Trademark E. R. Squibb & Sons.

The above formulations were administered to dogs, intramuscularly, at a concentration of 10 mg./kg. All of the dogs showed marked sedation (arousable), dlight ptosis and a cataleptic-like state on standing. The onset of these effects was about ½ hour for the preparations containing 2-chloro-11-(4-methyl-1-piperazinyl)-dibenz[b,f][1,4]oxazepine and 1½ hours for fluphenazine enanthate. The dogs appeared to be symptom free in 2 days. After 4 days all the dogs were challenged with apomorphine, subcutaneously, at a concentration of 0.25 mg./kg., to determine any residual drug effect (anti-emetic) not grossly observable. At this time (4 days post administration) only formulations II and IV gave complete protection against emesis.

Another experiment was done in Cebus monkeys, using the same formulations. The symptoms observed were marked sedation, catalepsy (arousable), calming, loss of agressiveness and loss of the flight reaction. The onset of effect was less than ½ hour for the formulations containing 2-chloro-11-(4-methyl-1-piperazinyl)-dibenz[b,f][1,4]oxazepine and about 1 hour for fluphenazine enanthate. The duration of effect was 3 days for Formula I, 5 days for II, and 4 days for III. The monkey given fluphenazine enanthate was markedly sedated on the fifth day.

The above tests show the prolonged action of Formula II and III containing an active compound of this invention in sesame oil, with and without aluminum monostearate.

The results shown in Table I compare the duration of action of 2-chloro-11-(4-methyl-1-piperazinyl)-dibenz[b,f]-[1,4]oxazepine base and pamoate in gelled and ungelled formulations and indicate that the gelling process caused a prolonged effect (P=0.05) for the low dose (5 mg./kg.) of 2-chloro-11-(4-methyl-1-piperazinyl)-dibenz[b,f][1,4]oxazepine base and for the high dose (10 mg./kg.) of 2-chloro-11-(4-methyl-1-piperazinyl)-dibenz[b,f][1,4]oxazepine pamoate. There was no significant differences between 2-chloro-11-(4-methyl-1-piperazinyl)-dibenz[b,f][1,4]oxazepine base and pamoate in the ungelled formulations given in equivalent doses.

It is concluded that the durations of action for both 2-chloro-11-(4-methyl-1-piperazinyl)-dibenz[b,f][1,4]-oxazepine base and pamoate are slightly, but significantly, prolonged when formulated in gelled sesame oil. 2-Chloro-11-(4-methyl-1-piperazinyl)-dibenz[b,f][1,4]oxazepine base and 2-chloro-11-(4-methyl-1-piperazinyl)-dibenz[b,f][1,4]oxazepine pamoate appear to be equal in duration of action. The pamoate formulation has an advantage over 2-chloro-11-(4-methyl-1-piperazinyl)-dibenz[b,f][1,4]oxazepine base, but only when gelled.

TABLE I

Duration of Catalepsy in Rats ($ET_{50}$ = time for 50% of the rats to remain cataleptic

| Parenteral Formulations of 2-Chloro-11-(4-methyl-1-piperazinyl)dibenz-(b,f][1,4]oxazepine base vs. Pamoate | I.M. mg./kg. | $ET_{50}$ (95% C.L.), Hours |
|---|---|---|
| Base | 5 | 56 (44–66)++ |
| (2% solu. - oil) | 10 | 79 (64–104) |
| Base | 5 | 93 (71–116)* |

TABLE I-continued

Duration of Catalepsy in Rats ($ET_{50}$ = time for 50% of the rats to remain cataleptic)

| Parenteral Formulations of 2-Chloro-11-(4-methyl-1-piperazinyl)dibenz-(b,f][1,4]oxazepine base vs. Pamoate | I.M. mg./kg. | $ET_{50}$ (95% C.L.), Hours |
|---|---|---|
| (2% solu. - gelled oil) | 10 | 70 (estimated)+ |
| Pamoate | 10 | 76 (52–89)+ |
| (2% susp. - oil) | 20 | 82 (60–96) |
| Pamoate | 5 | 88 (55–315) |
| (2% susp. - gelled oil) | 10 | 135 (110–188)** |

Statistical comparison of the above data showed that 2-chloro-11-(4-methyl-1-piperazinyl)dibenz[b,f][1,4]oxazepine pamoate suspended in gelled oil (10 mg./kg.)** produced the longest duration of catalepsy (P=0.05) with the exception of 2-chloro-11-(4-methyl-1-piperazinyl)dibenz[b,f][1,4]oxazepine base (5 mg./kg.)* solubilized in gelled oil. ++Significantly (P=0.05) lower than other $ET_{50}$'s except+.

Other Formulations Studied:

| 2-chloro-11-(4-methyl-1-piperazinyl)-dibenz[b,f][1,4]oxazepine Pamoate | | |
|---|---|---|
| | 5 | 69 (44–86) |
| (5% susp. - oil) | 10 | 75 (52–92) |
| Stearate | 5 | 56 (38–67) |
| (2% solu. - oil) | 10 | 78 (50–120) |
| Stearate | 5 | 53 (26–70) |
| (2% solu. - gelled oil) | 10 | 67 (estimated) |
| Succinate | 5 | 70 (estimated) |
| (2% susp. - oil) | 10 | 70 (estimated) |
| Enanthate | 5 | 53 (26–70) |
| (2% solu. - oil) | 10 | 62 (40–82) |
| (10% solu. - oil) | 10 | 72 (51–85) |
| Prolixin | 5 | 87 (74–102) |
| (2.5% solu. - oil | 10 | 114 (94–158) |

We claim:

1. A pharmaceutical composition for parenteral administration characterized by prolonged duration of activity, which comprises as the main active ingredient therein at a concentration of about 50 mg./ml. to about 400 mg./ml. the pamoate salt of 2-chloro-11-(1-piperazinyl)dibenz[b,f][1,4]oxazepine or the pamoate salt of 2-chloro-11-(4-methyl-1-piperazinyl)dibenz[b,f][1,4]oxazepine, in an injectable oil containing a gelling agent at a concentration of from about 10 mg./ml. to about 100 mg./ml.

2. A composition according to claim 1 wherein the main active ingredient is 2-chloro-11-(1-piperazinyl)-dibenz[b,f][1,4]oxazepine pamoate and the injectable oil is sesame oil.

3. A composition according to claim 1 wherein the main active ingredient is 2-chloro-11-(4-methyl-1-piperazinyl)-dibenz[b,f][1,4]oxazepine pamoate and the injectable oil is sesame oil.

4. A composition according to claim 1 wherein the main active ingredient is 2-chloro-11-(1-piperazinyl)-dibenz[b,f][1,4]oxazepine pamoate, the injectable oil is sesame oil and the gelling agent is aluminum monostearate.

5. A composition according to claim 1 wherein the main active ingredient is 2-chloro-11-(4-methyl-1-piperazinyl)-dibenz[b,f][1,4]oxazepine pamoate, the injectable oil is sesame oil and the gelling agent is aluminum monostearate.

6. A method of treating central nervous system disorders in a warm-blooded animal which comprises parenterally administering to said animal a therapeutically effective amount of a pharmaceutical composition for parenteral administration containing as the main active ingredient therein at a concentration of about 50 mg./ml. to about 400 mg./ml. the pamoate salt of 2-chloro-11-(1-piperazinyl)dibenz[b,f][1,4]oxazepine or the pamoate salt of 2-chloro-11-(4-methyl-1-piperazinyl)dibenz[b,f][1,4]oxazepine, in an injectable oil and a gelling agent at a concentration of about 10 mg/ml.

7. A method according to claim 6 wherein the main active ingredient is 2-chloro-11-(4-methyl-1-piperazinyl)-dibenz[b,f][1,4]oxazepine pamoate, the injectable oil is sesame oil and the gelling agent is aluminum monostearate.

8. A method according to claim 6 wherein the main active ingredient is 2-chloro-11-(1-piperazinyl)-dibenz[b,f][1,4]oxazepine pamoate, the injectable oil is sesame oil and the gelling agent is aluminum monostearate.

* * * * *